United States Patent [19]

Davis

[11] Patent Number: 4,951,683
[45] Date of Patent: Aug. 28, 1990

[54] DEVICE FOR DETECTING KERATOCONJUNCTIVITIS SICCA

[76] Inventor: Jeffrey P. Davis, 2751 Chamberlain Ave., Madison, Wis. 53705

[21] Appl. No.: 300,860

[22] Filed: Jan. 19, 1989

[51] Int. Cl.$^5$ .............................................. A61B 5/00
[52] U.S. Cl. ..................................... 128/734; 128/632
[58] Field of Search ..................... 128/734, 645–652, 128/632, 635–636, 639, 642–644

[56] References Cited

U.S. PATENT DOCUMENTS

| | | | |
|---|---|---|---|
| 2,852,739 | 9/1958 | Hansen | 128/734 X |
| 3,382,434 | 5/1968 | Gibson, Jr. et al. | 128/734 X |
| 3,680,028 | 7/1972 | Black et al. | 128/645 X |
| 3,769,961 | 11/1973 | Fatt et al. | 128/635 |
| 4,109,648 | 8/1978 | Larke et al. | 128/639 |
| 4,269,197 | 5/1981 | Gilbard | |
| 4,365,637 | 12/1982 | Johnson | 128/734 |
| 4,577,640 | 3/1986 | Hofmeister | 128/734 X |
| 4,690,148 | 9/1987 | Hess | 128/639 |

OTHER PUBLICATIONS

Zetek Inc. Brochure "Introducing the Cue Ovulation Predictor"—undated.
Fisher Scientific—Catalogue—"pH/pX (Electrodes)", undated.
"Osmolarity of Tear Microvolumes in Keratoconjunctivitis Sicca", Jeffrey Gilbard et al, Arch Ophthalmol, vol. 97, Apr. 1978.
Aboul-Ela, et al—"Relationships Between Intravaginal Electrical Resistance, Cervicovaginal Mucus Characteristics & Blood et al"—Animal Reprod. Science, pp. 259–273, 1982/83.
Swanson et al—A Model for Skin–Electrode Impedance—pp. 117–128.
John G. Webster—Encyclopedia of Medical Devices and Instrumentation—vol. 1–4, pp. 896, 1063–1066, 1671–1672, 1681–1682.

Primary Examiner—Angela D. Sykes
Attorney, Agent, or Firm—Bielen, Peterson & Lampe

[57] ABSTRACT

A device for detecting keratoconjunctivitis sicca (KCS) utilizing a probe including a body having an end portion. A plurality of electrical contacts are mounted in spaced configuration at the end portion of the probe body for simultaneous contact with the tear fluid of the ocular conjunctiva, or components thereof. An electrical potential is applied to at least one of the plurality of the electrical contacts and electrical activity, such as conductance, between the one electrical contact to another electrical contact is measured relative and the interposed tear fluid.

14 Claims, 2 Drawing Sheets

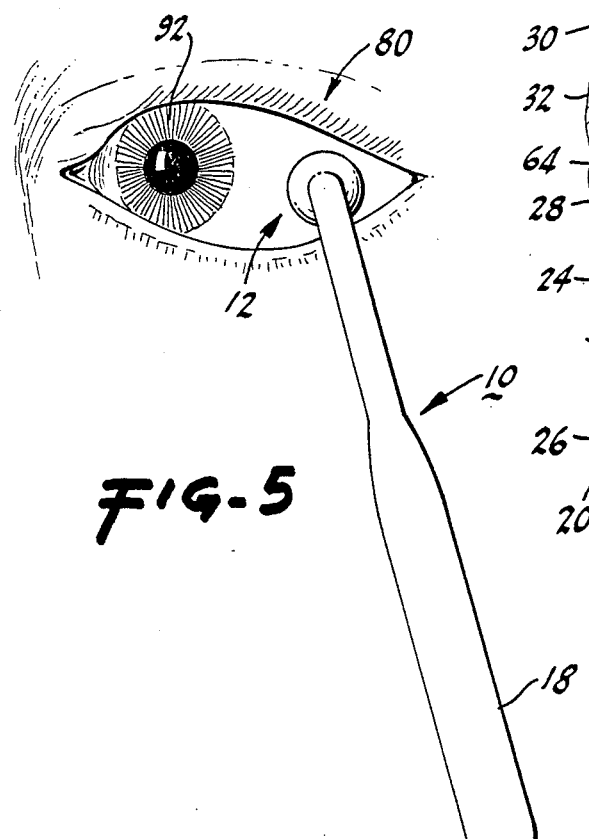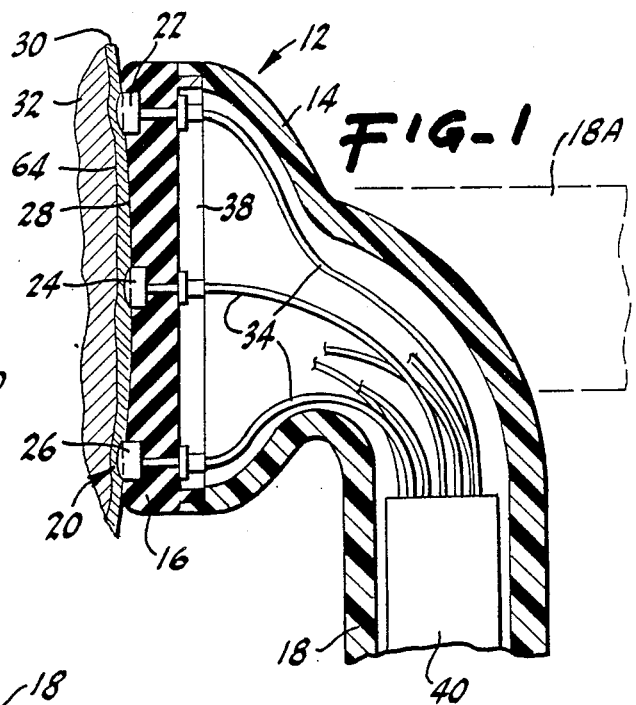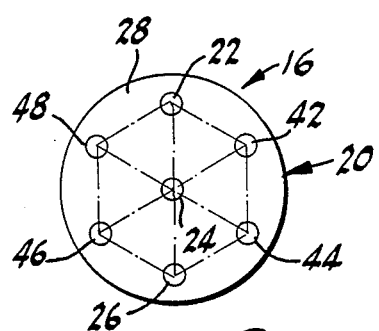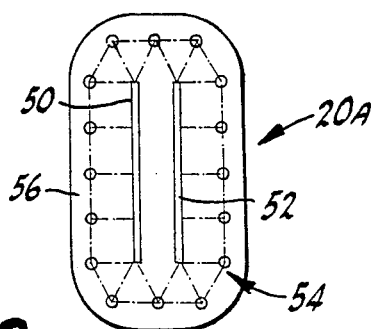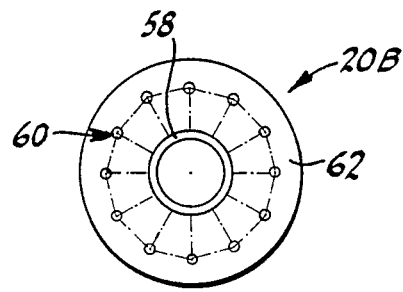

DEVICE FOR DETECTING KERATOCONJUNCTIVITIS SICCA

BACKGROUND OF THE INVENTION

The present invention relates to a novel and useful device for primarily detecting mammalian keratoconjunctivitis sicca.

Keratoconjunctivitis sicca (KCS) or "dry eye" is an ophthalmic condition defined by an insufficiency or imbalance of one or more of the ocular fluid components of an eye. Such imbalance may involve aqueous tear fluid, conjunctival mucin, and/or tear fluid lipid. KCS frequently threatens ocular anatomic integrity, often causing conjunctival and corneal erosion. "Dry eye" is a finding in about 25% of Sjogren's syndrome, which most often occurs in women past the age of 45 years. Sjogren's syndrome often detrimentally affects the immune system of the body; thus early detection and treatment is important. It has been estimated that several million persons in the United States alone are affected by KCS. 90% of such KCS cases are due to Sjogren's syndrome. KCS also commonly afflicts several canine species.

A moderate case of KCS is normally first noted clinically as ocular surface "burning", itching, prickly corneal pain, altered vision, accumulation of mucus threads, occasional overflow of reflex tears, and other forms of ocular surface discomfort due to the noted aberrance of tear fluid components.

The Schirmer tear production test is now one of the two mainstay diagnostic tests for KCS, Such test consists of measuring the length of wetting of a standardized filtered paper strip which is notched and folded over the eyelid margin, into the inferior fornix, and may be performed with or without anesthetic. The Schirmer test is cumbersome and time consuming, as well as inaccurate. Reproducibility of the Schirmer test, in the hands of the average practitioner, varies between 25% and 50%.

Rose bengal ocular surface staining is the other mainstay test employed to detect KCS. This test, which is somewhat time consuming, stains devitalized cells and mucin in the tear film. Rose bengal staining, although moderately accurate, is not completely diagnostic of KCS, since it does not detect "early" cases, which represent a significant fraction of KCS occurence. Rose bengal staining does effectively uncover "later" stages of KCS which are termed moderate to severe, but such test does not grade the fundamental tear osmolality defect.

The tear "break up time" test may also be used to detect KCS. In such a test, a fluorescein strip is used to initially stain the tear film and the time to first corneal tear film breakup is noted under slit lamp biomicroscope observation. Even with repeat measurements, the accuracy is highly variable in this test.

Reference is made to U.S. Pat. No. 4,269,197 to Gilbard in which a micropipette is employed to take human tear samples for measurement of tear osmolarity, generally by freezing point depression determination. Such a meticulous, time consuming test is prohibitive in a routine clinical setting and requires a relatively long time period between obtaining a tear fluid sample and analysis of the same. Also, most eye care practitioners do not possess the freezing point depression apparatus required for this test. Gilbard et al in an article "Osmolality of Tear Microvolumes In Keratoconjunctivitis Sicca" Arch Ophthalmol. 1978,96, 677–81, correlated measurement of tear osmolarity/osmolality to the existence and clinical severity of KCS in patients.

Lingual and vaginal muscosal surface conductance measurements have been taken by in vivo tissue contacting devices to acertain the time of mammalian ovulation. Conductance in the vaginal mucus have been observed and linked largely to sodium and chloride ionic activity, therein. An article by Aboul-ela et al entitled "Relationships Between Intravaginal Electrical Resistance, Cervicovaginal Mucus Characteristics and Blood Progesterone and LH" describes measurements of intravaginal electrical resistance made on Hereford-Friesian heifers. In addition, a mucus epithelial conductance-based ovulation predictor or monitor is manufactured by Zetek Inc. of Aurora, Colo. under the name "Cue" for human use.

Skin electrical impedance has been extensively gauged using aqueous gel coatings and contact electrodes in conjunction with electrocardiogram measurements. For example, an article entitled "A Model For Skin-Electrode Impedance" by Swanson et al, describes such measurements.

Also, ion specific electrodes for solutions have been developed. For example, Fisher Scientific Company of Pittsburg, PA. describes such electrodes under the designation "pH/pX". Further, ion-selective membranes are defined in the "Encyclopedia of Medical Devices and Instrumentation", Edited by Webster, J. for use in clinical and medical fields.

There are no known devices or methods for measuring the electrical or specific ion activity of the ocular fluid in its natural condition of coating the ocular surface in vivo.

The accurate measurement of human ocular tear fluid osmolarity with a simple, rapid method and apparatus would be an important advance in the medical field.

SUMMARY OF THE INVENTION

In accordance with the present invention a novel and useful device for measuring in vivo tear fluid osmolarity/osmolality and detecting a "dry eye" (KCS) condition is provided.

The present invention employs a probe including a body which has an end portion. The probe may also possess a handle or other like member for manipulating the same relative to a living animal eye. The handle surface may include indents compatible with the controlling fingertips of the operator. The body end portion may also include a surface which generally conforms to the curved surface structure of an eye, especially the conjunctival portion of the eye. In certain aspects of the present invention the end portion of the ocular contact probe may include a solid, liquid, or polymeric membrane which may form a chamber within the probe body. Such membrane may be porous or reactive to a specific ion or a group of ions found in the tear fluid.

In one embodiment of the invention a plurality of contacts are also provided herein and are mounted in spaced configuration at the end portion of the probe body. In such a formation, the plurality of electrical contacts are intended to simultaneously communicate with the ocular tear fluid in situ. The plurality of contacts may include six evenly spaced contacts in a hexagonal configuration, and further define one contact lying at the center of the hexagon. The central contact would be provided an electrical potential through suitable means. In other embodiments, the electrical contact receiving the potential may be a circular band, be split into two parallel strips, or formed into other configurations.

Means is also included in the present invention for measuring electrical activity between the electrical contact provided with an electrical potential and at least one other electrical contact while such contacts are communicating with or touching the ocular tear fluid in situ. It is conceived that the electrical contact having an electrical potential may be switched among the plurality of contacts to avoid electrode polarization problems. Likewise, any of the plurality of contacts may be employed in the measuring of electrical activity, eg: conductance, resistance, etc. emanating from the electrical contact having the electrical potential. Where the end portion of the probe body includes an ion selective membrane forming a chamber, the specific ion activity of interest may be measured against an internal reference by an outside meter. Of course, an ion selective membrane may quantify the solution activity of a particular tear fluid ion in other ways, known in the art.

The electrical activity measured, eg: resistance, conductance, capacitance, potential and the like, may be translated into a measurement of the tear film osmolarity/osmolality or other like quantity indicating total ion activity in the ocular tear fluid. Such ionic activity is easily translated into a physiologic diagnosis of KCS.

It may be apparent that a novel and useful device for detecting KCS in an eye has been described.

It is therefore an object of the present invention to provide a device for detecting KCS which diagnoses such condition near the initiation of the same.

It is another object of the present invention to provide a device for detecting KCS which is quickly and simply used in a routine clinical setting and produces extremely accurate results.

Another object of the present invention is to provide a device for detecting KCS which is light in weight and fully portable.

A further object of the present invention is to provide a device for detecting KCS which delivers reproducable results, permitting comparisons of measurements obtained over specific time periods, on any given individual.

A further object of the present invention is to provide a device for detecting KCS which is non-invasive of the body structure, especially the eye.

Yet another object of the present invention is to provide a device for detecting KCS in the eye which is inexpensive to manufacture and durable over lengthy periods of continued use, thus rendering such device available to a large number of users.

Yet another object of the present invention is to provide a device for detecting KCS which would permit clinical testing potential of artificial tear products and/or "dry eye" therapeutic medications.

Another object of the present invention is to provide a device and method for the detection of KCS which would greatly expedite clinical diagnosis of "dry eye" cases and expand the sensitivity range for KCS detection from the present standard.

A further object of the present invention is to provide a device for detecting KCS in the eye which would be simple to integrate into existing equipment used by eye care practitioners.

Yet another object of the present invention is to provide a device and method for determining KCS in an eye which would aid in determining the possibility of such condition, occurring or existing subclinically in particular groups of persons, such as would-be contact lens wearers.

The invention possesses other objects and advantages especially as concerns particular characteristics and features thereof which will become apparent as the specification continues.

BRIEF DESCRIPTIONS OF THE DRAWINGS

FIG. 1 is a sectional view of an embodiment of the present invention showing an alternate embodiment of the handle portion in phantom.

FIG. 2 is a front elevational view of the end surface of the probe of the present invention depicting a particular pattern of electrical contacts.

FIG. 3 is a front elevational view of the end surface of the probe of the present invention depicting another pattern of electrical contacts.

FIG. 4 is a front elevational view of the end surface of the probe of the present invention depicting yet another pattern of electrical contacts.

FIG. 5 is a rear elevational view of the device in use on a human eye with a portion of a electrical circuitry shown in schematic block diagram format.

Figure 6:
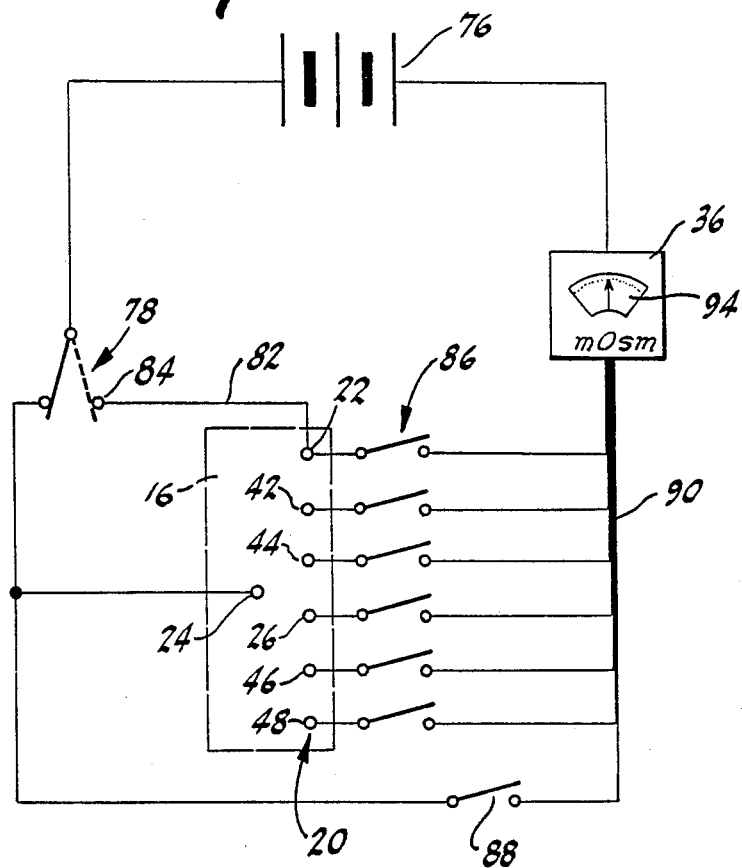
FIG. 6 is a schematic view of a typical circuitry usable with the embodiment shown in FIGS. 1 and 2.

For a better understanding of the invention reference is made to the following detailed description of the preferred embodiments thereof which should be referenced to the hereinabove described drawings.

DESCRIPTION OF THE PREFERRED EMBODIMENT

Various aspects of the present invention will evolve from the following detailed description of the preferred embodiments of the present invention which should be referenced to the prior described drawings.

The invention as a whole is shown in the drawings reference character 10. The device 10 for detecting the condition known as keratoconjunctivitis sicca (KCS) may be described as a tear conductance osmometer, details of which will be described hereinafter. Device 10 includes as one of its elements a probe 12, FIG. 1, having a body 14 with an end portion section 16. Body 14 may be constructed of any rigid or semi-rigid material such as plastic, metal, ceramic compositions and the like. As depicted in FIG. 1, body 14 is formed of a non-conducting material such as plastic. A handle 18 is further depicted in FIGS. 1 and 5 as being angularly disposed relative to end portion 16. Handle 18 may also be formed in axial alignment with end portion 16 as depicted by handle 18A, shown in phantom on FIG. 1. Either handle 18 or 18A may include a knurled, contoured gripping surface. In addition, probe body 14 may take the form of a contact lens without handle 18.

The device 10 also includes a plurality of electrical contacts 20, FIGS. 1–4, mounted in spaced configuration. As shown in FIG. 1, electrical contacts 22, 24 and 26 are fixed in end portion 16, but have a convex surface that extends beyond non-conducting end surface 28 of end portion 16. It is intended that plurality of electrical contacts simultaneously communicate with or touch tear fluid or film 30 which coats conjunctiva 32. A plurality of conductors or wires 34 lead from plurality of contacts 20 to conductance meter 36, depicted in block form on FIGS. 5 and 6. It should be noted that plurality of contacts 20 shown in FIG. 1 are wedged into recess 38 molded into end portion 16 of probe body 14. Sheath 40 mechanically encompasses plurality of conductors 34. Contacts 20 may be constructed of any high conductance, low corroding material such as gold, platinum, stainless steel and the like.

Turning to FIGS. 2–4, several patterns of plurality of electrical contacts 20 are illustrated. In FIG. 2, contacts 22, 26, 42, 44, 46, and 48 are arranged in a regular hexagonal pattern; contact 24 serving as the center of such pattern. Thus, contact 24 is equidistant from any of the other contacts serving to define the periphery of a hexagon. It should also be observed, that any peripheral contact would be equidistant from three other contacts.

With reference to FIG. 3, plurality of contacts 20A may take the form of conductive strips 50 and 52 surrounded by multiplicity of peripheral contacts 54. Non-conducting end surface 56 would take the shape of a rectangle having rounded corners. FIG. 4 utilizes a ring contact 58 surrounded by multiplicity of peripheral contacts 60. Concentric rings or bands such as ring 58 may also be employed. Non-conducting end surface 62 thereof is circular as is end surface 28 shown in the embodiments depicted in FIGS. 1 and 2. For example, the overall diameter of end surface 28 would range between (7) and (12) millimeters with a typical spacing between contacts being (2) millimeters. It should be mentioned that end surfaces such as end surfaces 28, 56 and 60 may take a variety of shapes to accommodate the eyelid fissure and the layout of electrodes 20. In this regard, end surface 28, is concave to a degree necessary to conform to the outer surface 64 of ocular conjunctiva 32. It is anticipated that surfaces 56 and 62, FIGS. 3 and 4 would also be concave to generally conform to the outer surface 64 of conjunctiva 32.

Figure 7:
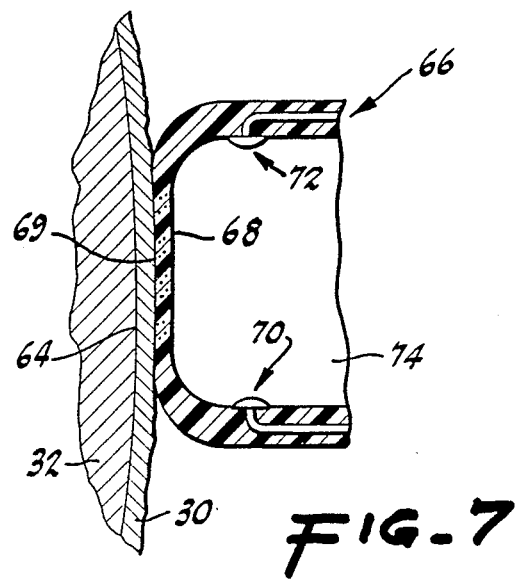
FIG. 7 is a sectional view depicting the end of a probe body which may be employed in the present invention having a ion-selective membrane forming a chamber.

Turning to FIG. 7, a probe end 66 of a different embodiment is depicted. Probe end 66 includes a porous membrane 68 which is ion selective i.e. permitting only a certain ion or ions to pass therethrough i.e. sodium, potassium, chloride, calcium, and the like. Membrane end surface 69, generally conforms to the surface 64 of conjunctiva 32, although only good contact with fluid 30 is required. The equilibruim ionic activity of a particular ion in chamber 74 may be measured quickly and accurately by more than one method. For example, the chloride ion is measured against an internal reference electrode by a portable meter external to the electrode. Also, sodium ion activity is determined at a contacted liquid surface by the potential it generates in reacting with a "solid" calibrated ion selective membrane. It should also be noted that membrane 68 may take the form of a simple ion selective electrode prior described, without chamber 74.

With reference to FIG. 6, it may be seen that means 76, in the form of a 0.1–10 volt DC power supply is employed for providing an electrical potential to one of the plurality of the contacts 20. Such potential may be electronically pulsed, eg: 50–1000 Hz. In the embodiment shown, double throw switch 78 may be used to place a potential on contact 24, as depicted. In such a case contacts 22, 42, 44, 26, 46, and 48 would receive any electrical current traveling through tear fluid 30 when probe 12 is placed in such fluid 30 enveloping the conjunctiva 32 of eye or eyeball 80, FIG. 5. However, activating electrical leg 82 by throwing switch 78 to contact 84 activates contact 22, a peripheral contact in the embodiment depicted in FIG. 2. In such a case, switches associated with contacts 24, 42 and 48 of plurality of switches 86, would also be closed. It is to be noted that switch 88 associated with contact 24 would be simultaneously closed with the closing of switch 78 onto contact 84. In other words, a relay would suffice as a substitute for switches 78 and 88 in this regard. Leg 90 represents a multiplicity of conductors, originating with each of the plurality of switches 86 associated with contacts 22, 42, 44, 26, 46, and 48, it being understood that contact 24 may be substituted for contact 22 in this grouping.

Conductance meter 36 receiving the current from plurality of contacts 86 would, thus, determine the conductivity or of tear fluid 30 eg: 20–2000 microamps. In certain cases such measurement could be in units of voltage. This measurement is easily translated by mathematical tables into a measurement of the tear fluid osmolality (mOsm). It has been determined that the average normal human tear meniscus osmolality (tonicity) is 302 mOsm. "Dry eye" normally begins with a reading greater than 311 mOsm. Moderately severe dry eye exhibits an average tear tonicity of 343 mOsm, while severe dry eye exhibits a value as high as 360 mOsm. Such results have been established by J. P. Gilbard, previously discussed. Any readout 94, analog or digital, on conductance meter 36 may be programmed to read the mOsm value rather than the electrical activity value, eg: amperage.

In operation, the patient being examined would be asked to gently yet completely blink the lids of eye 80 a number of times to adequately mix the meniscus tear fluid with ocular surface tear fluid 28 before the contact of probe 12 on conjunctiva 32 is effected. The operator would then gently and securely touch the plurality of contacts 20, 20A, 20B, or membrane 68 to an area of conjunctiva 32 on either side of, or above or below the cornea 92 of eye 80, FIG. 5. Plurality of contacts 20, 20A, 20B, or membrane 68 substantially make contact with fluid 30, since end surface 28 of end portion 16 substantially conforms to the bulbar conjunctival curvature. After this procedure, conductance meter 36 would read the conductance translated to osmolality of tear fluid 30 between pairs of equidistant contacts. Probe 12 may selectively employ sodium, potassium, chloride, calcuim and like ions present in tear film 30, in this regard. As heretofore described, contacts, such as contacts 24 and 22 of FIG. 6, may be repeatedly interchanged to produce the potential necessary to obtain tonicity values readable on conductance meter 36 readout 94. This interchange of contacts may be necessary to obviate electrode polarization error and to obtain measurements of osmolality in several areas of the conjunctiva. Further, such multiple readings may be automatically averaged and recorded. In addition, multiple readings may be obtained and compared for reproducibility before display. It should be noted, that probe 12 may be precisely positioned by affixing it to an existing biomicroscope normally found in ophthalmologic and optometric examining rooms.

While in the foregoing embodiments of the invention have been set forth in considerable detail for the purpose of making a complete disclosure of the invention it may be apparent to those of ordinary skill in the art that numerous changes may be made in such detail without departing from the spirit and principle of the invention.

What is claimed is:

1. A device for detecting keratoconjunctivitis sicca in an eye, being usable with an ocular tear fluid on the eyeball in vivo, comprising
   a. probe means for contacting the ocular tear fluid on the eyeball, said probe means including a body, said body having an end portion with an end surface capable of directly contacting the ocular tear fluid coating the eyeball;
   b. a plurality of electrical contacts being mounted in spaced configuration and being accessible at said end surface of said end portion of said body to simultaneously communicate with the ocular tear fluid coating the eyeball,
   c. means for providing an electrical potential on one of said plurality of electrical contacts; and
   d. means for measuring electrical activity between said one electrical contact and another of said plurality of electrical contacts while said electrical contacts communicate with the ocular tear fluid on the eyeball in vivo.

2. The device of claim 1 in which said end portion includes an exterior surface which is concave.

3. The device of claim 1 in which said end portion includes an exterior surface which is curved to generally conform to the outer surface of the eye.

4. The device of claim 1 in which said plurality of electrical contacts includes six contacts in regular hexagonal configuration, and one of said contacts lying at the center of said hexagon.

5. The device of claim 1 in which said one contact is circular.

6. The device of claim 1 in which said one contact is split into a first and second linear portion.

7. The device of claim 1 in which said end portion of said probe includes a membrane forming a chamber in said probe body.

8. The device of claim 1 which additionally includes means for selectively translating said measured electrical activity into a measurement of tear film osmolarity and osmolality.

9. The device of claim 1 in which said probe end portion includes an end surface conforming to the curvature of the eye, said plurality of contacts lying adjacent said curved end surface of said probe end portion.

10. A method measuring a characteristic of ocular tear fluid on the eyeball in vivo comprising the steps of:
    a. mechanically applying a probe to the tear fluid on the eyeball, said probe including a body having an end portion, with an end surface and a plurality of electrical contacts being mounted in spaced relationship and being accessible at said end surface of said end portion of said probe body, said electrical contacts communicating with the tear fluid; on the eyeball
    b. electrically applying potential to one of said plurality of electrical contacts; and
    c. measuring the electrical activity between said one electrical contact and another of said plurality of electrical contacts while said electrical contacts communicate with the ocular tear fluid on the eyeball in vivo.

11. The method of claim 10 which additionally comprises the step of selectively translating said measurement of electrical activity into a measurement of tear fluid osmolarity and osmolality.

12. A method of measuring a characteristic of eye tear fluid in vivo on the eyeballs, comprising the steps of:
    a. mechanically applying a probe to the in situ tear fluid on the eyeball, said probe including an ion specific electrode; and 13. A device for detecting keratoconjunctivitis sicca in an eye, being usable with an ocular tear fluid on the eyeball, comprising;
    a. a probe including a body, said body having an end portion with an end surface capable of contacting the ocular tear fluid in vivo on the eyeball, said end surface of said probe end portion generally conforming to the contour of a portion of the eyeball;
    b. means for detecting ionic electrical activity of the tear fluid in the vicinity of the end surface of said probe end portion; and
    c. means for metering said ionic electrical activity in the tear fluid.

14. The device of claim 13 in which said means for detecting ionic electrical activity includes an ion-specific electrode.

* * * * *